United States Patent [19]
Reynell

[11] Patent Number: 5,958,756
[45] Date of Patent: *Sep. 28, 1999

[54] METHOD AND APPARATUS FOR TREATING WASTE

[76] Inventor: Christopher Paul Reynell, Windover Farm, Longstock, Stockbridge, Hampshire, S020 6DJ, United Kingdom

[*] Notice: This patent issued on a continued prosecution application filed under 37 CFR 1.53(d), and is subject to the twenty year patent term provisions of 35 U.S.C. 154(a)(2).

[21] Appl. No.: 08/875,461

[22] PCT Filed: Jan. 26, 1996

[86] PCT No.: PCT/GB96/00184

§ 371 Date: Jul. 28, 1997

§ 102(e) Date: Jul. 28, 1997

[87] PCT Pub. No.: WO96/23054

PCT Pub. Date: Aug. 1, 1996

[51] Int. Cl.[6] ............................ C12S 13/00; C05F 17/00
[52] U.S. Cl. .................. 435/262; 435/290.4; 435/294.1; 71/9; 71/10; 210/603; 210/612
[58] Field of Search ................................. 435/262, 262.5, 435/289.1, 290.1, 290.2, 290.4, 294.1, 300.1; 71/8–10; 210/603, 605, 612

[56] References Cited

U.S. PATENT DOCUMENTS

| | | |
|---|---|---|
| 2,458,431 | 1/1949 | Schlenz . |
| 3,214,195 | 10/1965 | Zahuranec et al. . |
| 4,414,335 | 11/1983 | Kipp, Jr. . |
| 4,885,094 | 12/1989 | Srinivasan et al. . |
| 5,342,097 | 8/1994 | Hanson . |

FOREIGN PATENT DOCUMENTS

| | | |
|---|---|---|
| 74312/91 | 4/1991 | Australia . |
| 0 023 176 | 1/1981 | European Pat. Off. . |
| 0 052 049 | 5/1982 | European Pat. Off. ............ 435/300.1 |
| 0 198 465 | 10/1986 | European Pat. Off. . |
| 898669 | 5/1945 | France . |
| 2121934 | 8/1972 | France ............................... 435/290.1 |
| 2346448 | 10/1977 | France ............................... 435/300.1 |
| 2461747 | 2/1981 | France ............................... 435/300.1 |
| 2505603 | 11/1982 | France . |
| 25 35 756 | 2/1977 | Germany ........................... 435/290.2 |
| 7902752 | 10/1980 | Netherlands ....................... 435/290.2 |
| 8202737 | 2/1984 | Netherlands ....................... 425/290.1 |
| 2 230 004 | 10/1990 | United Kingdom . |
| 82/00300 | 2/1982 | WIPO ................................ 435/300.1 |
| 92/12938 | 8/1992 | WIPO . |
| WO 96/23054 | 1/1996 | WIPO . |

OTHER PUBLICATIONS

English language translation of FR 2,121,934, Sep. 1998.

*Primary Examiner*—William H. Beisner
*Attorney, Agent, or Firm*—Howell & Haferkamp, LC

[57] ABSTRACT

A process for digesting solid waste material comprises collecting the waste from a first location in a solids digestion vessel and transporting it to a second location where a fluids digestion vessel is located. At least some of the fluid fraction from the fluids digestion vessel is fed to the solids digestion vessel so that anaerobic digestion of the solid waste occurs in the solids digestion vessel. At least some of the digested solid waste is recovered and the solids digestion vessel is preferably returned to the first location. The invention also provides apparatus for use in the process.

6 Claims, 3 Drawing Sheets

METHOD AND APPARATUS FOR TREATING WASTE

The present invention relates to a method and apparatus for treating waste, and particularly for treating solid and liquid waste in two stages.

Abattoirs, farms, food processing plants and the like regularly produce solid organic waste which needs to be treated in order to render it suitable for discharge into the environment.

One method which is known for digesting such waste is described in British patent number 2 230 004, the contents of which are hereby incorporated by reference. This document describes a two stage digestion process which uses an installation comprising a fluids digestion vessel and a solids digestion vessel which are connected together. The solids digestion vessel is in the form of a tower or other fixture which is located in or on the ground, and the fluids digestion vessel is an adjacent tank. Bacterially active waste is fed from the fluids digestion vessel into the solids digestion vessel until at least some of the solids have been sufficiently digested to be environmentally acceptable. The digested solids are then removed, perhaps for use as a soil conditioning agent, and a further batch of solids waste is added to the solids digestion vessel.

A problem with this process is that the organic waste material which is to be digested must be loaded onto a transport container where it is produced, and subsequently transferred from the transport container into the solids digestion vessel. Typically the waste producer uses a skip into which the waste is tipped for transport. The untreated waste often smells offensive, and it may be hazardous to health.

It is an object of the present invention to provide a process for digesting solid waste material which reduces the above mentioned problems, and apparatus for use in carrying out the process.

According to a first aspect of the present invention there is provided a process for digesting a solid waste material, which process comprises:

a. collecting waste material containing biodegradable solids in a solids digestion vessel at a first location;

b. transporting the solids digestion vessel to a second location at which is sited a source of organic material undergoing anaerobic bacterial digestion in a fluid phase digestion stage to produce a fluid fraction containing active bacteria;

c. feeding at least part of the fluid fraction from the fluid phase digestion stage into the solids digestion vessel to provide at least part of a fluid phase in the solids digestion stage; and d. recovering at least part of the environmentally more acceptable solids fraction from the solids digestion stage.

Preferably the process also includes the step of transporting the solids digestion vessel away from the second location. The solids digestion vessel is preferably transported back to the first location, although it may alternatively be transported to another site.

The fluid which is transferred from the fluid source may also transfer heat and/or nutrients to the solids digestion vessel.

By using a mobile solids digestion vessel the waste may be loaded directly into the vessel at source, thereby reducing the amount of materials handling necessary in the process. Furthermore, the vessel may be substantially sealed during transport so as to reduce the escape of odour into the environment.

An additional benefit is that the producer of the waste may readily have the treated waste returned to him in the same vessel. The treated waste may then be unloaded at leisure, and a new load of waste loaded into the vessel. This reduces the handling required for the solid waste products, and it ensures that the waste producer will receive back his own treated waste, and not someone else's treated waste of unknown origin and therefore unknown composition.

It is preferred that the solids digestion vessel is connected to the fluid source by a pipe or other conduit means so that the feeding of fluid from the fluid source to the vessel may be conveniently carried out. It would however be possible to feed the fluid to the solids digestion vessel by other means, for example in one or more buckets. For convenience hereinafter the invention will be described with reference to at least one connection for feeding fluid from the fluid source to the solids digestion vessel.

The solids digestion vessel may be either wholly or partially mobile by being mounted on, or part of, a vehicle, for example a container lorry or a rail bulk wagon.

The bacterial digestion is anaerobic, but aerobic digestion may additionally be used in the process. Some waste, for example abattoir waste, is preferably anaerobically digested for several days, and then subjected to aerobic digestion for some more days. For example abattoir waste may be anaerobically digested for seven days, and then aerobically digested for seven more days.

The preferred digestion times will be influenced by the nature of the waste which is being digested and the use to which the digested solids waste is to be put. For composting for example, it is preferred that anaerobic digestion is carried out for one to four days, and aerobic digestion from 10 to 25 days. For soil conditioning agents, typically anaerobic digestion will be maintained for four to nine days followed by 7 to 14 days of aerobic digestion. For convenience the invention will be described hereinafter with reference to anaerobic digestion.

Different types of bacteria predominate at different temperatures in anaerobic digestion of organic waste. Mesophilic bacteria operate in a relatively low temperature range, usually less than 40° C., and they have a relatively slow rate of digestion. Thermophilic bacteria work effectively in a higher temperature range, around 40° to 65° C. (the thermophilic range). Digestion in the higher temperature thermophilic range occurs more rapidly than in the lower temperature mesophilic range, and it gives better control or elimination of pathogens and parasitic organisms.

The solids digestion vessel is preferably provided with a heater for warming the waste material during the journey from the first location to the second location. This preheating of the waste helps to speed up the digestion process, thereby reducing the retention time. The heating may be particularly effective on long or slow journeys by allowing bacteria to operate in the thermophilic temperature range. The heater may also be used during the process, when the vessel is connected to the fluid source, to maintain a thermophilic temperature. The heater preferably heats the waste to a temperature in the range 20 to 80° C., and particularly preferably to the optimum thermophilic range. The optimum temperature range which will be used in practice will depend on the tolerance to temperature of the bacteria which are used to digest the waste. The heater may be independently powered, or it may be powered directly or indirectly (for example by the vehicle battery) from the dynamo of the vehicle engine. When the vessel is connected to the fluid source, its heater may be connected to an external power source to avoid draining the vehicle battery.

A plurality of vessels may each be connected to a single fluid source, thereby reducing the number of fluid source containers required whilst keeping the solid wastes substantially separate from each other. Each vessel may be directly connected to the fluid source, or the vessels may be connected to a common manifold which in turn is connected to the fluid source.

It is preferred that the total volume of the or all of the solids vessels is approximately equal to the volume of the fluid source.

The fluid source may comprise a conventional liquid digester; for example a completely stirred tank reactor.

The rate of completion of digestion of the solid waste material may be increased by agitation during the process. It is therefore preferred that the vessel is provided with means for agitating its contents. The agitating means may comprise any suitable means for separating or moving solids; for example a paddle for stirring, means for blowing gas through the solids, means for pushing liquid back up through the solids, or means for vibrating the waste solids. In a preferred embodiment the agitation means comprise means for blowing gas through the solids, because this may be achieved by recycling gas produced in the digestion process.

The agitating means is preferably mounted in the vessel and can be connected to an external supply of power or gas according to its mode of operation. A benefit of passing gas or liquid up through the solid waste to agitate it is that this may be achieved without the use of dedicated agitation means, thereby allowing a simplification of the design of the apparatus.

Anaerobic digestion produces a methane rich gas in the solids and fluid containing vessels. This gas can be used for agitation of the contents of either vessel or both vessels. It may also be used to equalise the pressure in both vessels, and to transfer heat from one vessel to another. Excess of gas may be used for energy generation, for example in a combined heat and power plant (CHP), or it can be flared off or vented to the atmosphere.

At least some of the fluid phase in the vessel is preferably returned from the vessel to the fluid source so that the fluid fraction recycles through the solids digestion stage. This recycling of liquid aids the transfer of heat, nutrients and active bacteria between the vessels.

Make up water, optionally containing nutrients for the bacteria and/or liquid organic wastes, may be added to the fluid source and/or the vessel as required.

All of the fluid connections between the fluid source and the vessel may be carried in a single umbilical or other connector. For example a single connector could carry two liquid and two gas pipelines, for two-way flow of liquid and gas between the fluid source and the connector. The use of a single connector for all the fluid connections is convenient. It is also safer than independently making all of the fluid connections, where forgetting to make one connection could lead to a loss of waste material and/or gas. For safety reasons it is preferred that the connector unsymmetrical so as to ensure that the connection may only be made when the connector is in a single correct orientation.

The flow of liquid and/or gas may occur by virtue of gravity or gas pressure, or one or more pumps may be used.

The environmentally more acceptable solids fraction is preferably recovered by stopping the passage of fluid from the fluid source to the vessel, and draining fluid from the vessel. The drained fluid is preferably returned to the fluid source. When the treated solids are adjudged sufficiently drained, the vessel may then be moved to a location remote from the fluid source, typically back to the first location, and the treated solid waste removed from the vessel. It would however be possible to remove the treated solid waste from the vessel at the second location. If it is convenient to handle the treated solid waste as a slurry rather than a solid, more of the fluid may be retained with the solid waste, or extra water may be added to the solid waste.

If the solid waste is to be aerobically digested after the anaerobic digestion stage this is preferably accomplished by stopping the inflow of fluid into the solids digestion vessel, and allowing fluid to drain out. Air is then pumped into the solids digestion vessel so that it percolates over the surface of the solid particles. The air may conveniently be introduced through a gas inlet pipe that has been used previously for feeding methane rich gas into the vessel. A layer of wood chips or other suitable odour absorbing material may optionally be laid over the top of the solid waste to reduce odorous emissions during the aerobic digestion stage.

The invention also provides apparatus suitable for carrying out the above described process.

Accordingly, a second aspect of the present invention provides anaerobic digestion apparatus comprising a fluids digestion vessel, a solids digestion vessel, and means for feeding fluid between the two vessels, characterised in that the solids digestion vessel is detachable from the fluids digestion vessel and transportable.

The solids digestion vessel is preferably provided with wheels for ease of transport, for example by being mounted on a trailer.

The invention will now be further described by way of example, with reference to the following drawings in which.

Figure 1:
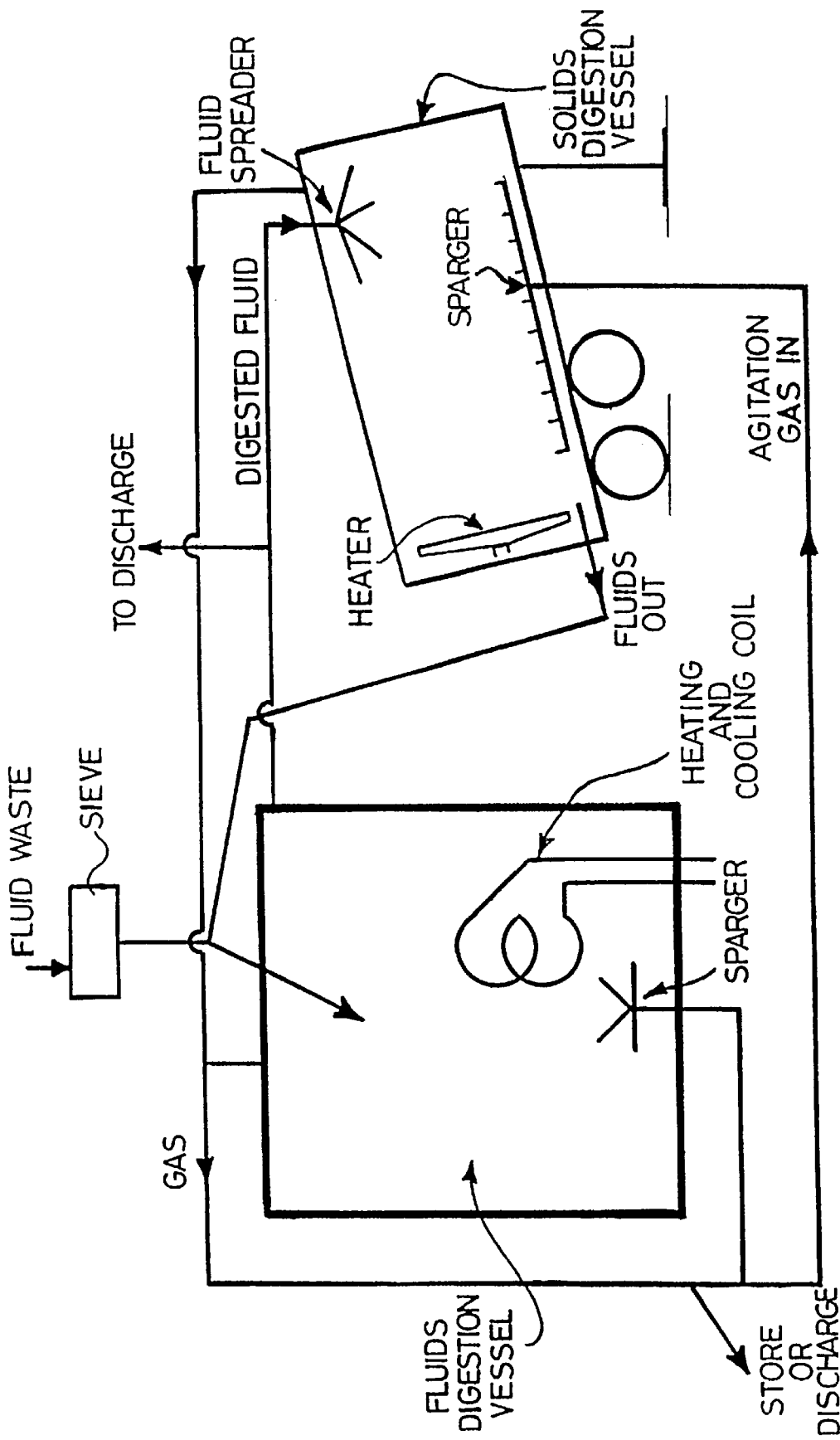
FIG. 1 is a diagrammatic flow diagram of the solid and fluid digestion stages of a process in accordance with a first embodiment of the invention.

The fluids digestion vessel shown in FIG. 1 is a conventional liquid digester. Fluid waste is passed into the fluids digestion vessel through a sieve to remove large particles, and the fluid is maintained at a temperature of around 55° C. by a heating and cooling coil. Cooling fluid is fed through the coil if the rate of digestion is too high so that the temperature is raised above a preset limit. Other temperatures could also be used; for example a temperature of around 35° C. could be used for digestion by mesophilic bacteria. The fluid waste is subject to anaerobic digestion in the presence of bacteria to provide an output which is biologically active, but in which much of the environmentally unacceptable material has been converted into acceptable material and methane gas. Some of the gas produced by the digestion process may be returned to the fluids digestion vessel via a sparger to help agitate the fluid. The fluid digestion stage will typically require the presence of a bacterial inoculum to initiate digestion, and this may be provided by the addition of partially treated sewage sludge in the initial material. However, the fluid digestion is preferably operated continuously, and material is recycled in the process, so that it is usually only necessary to provide an inoculum during start up of the process, or following a period of shut down.

A solids digestion vessel, here shown as a container lorry trailer, has been loaded with solid waste material at a remote location. The solids digestion vessel has been transported by road to the site of, and adjacent to, the fluids digestion vessel. A heater is mounted in the solids digestion vessel, and maintains the temperature of the solid waste at around 55° C. The heater is powered by the lorry battery in transit, and by an external power source when the vessel is connected to the fluids digestion vessel.

Connections are made between the solids digestion vessel and the fluids digestion vessel for the passage of fluid from the fluids digestion vessel to the solids digestion vessel, and vice versa so that the fluid fraction recycles through the solid waste. The fluid input to the solids digestion vessel is preferably via one or more spargers located at the top of the solids digestion vessel to assist uniform distribution of fluid across the surface of the solid waste. The fluid percolates down the solids digestion vessel and covers the surfaces of the solids within the vessel, thereby subjecting the solids to bacterial digestion by the bacteria within the fluid. The fluid need not flow over the solids under gravity, but may be pumped to increase the flow rate. It is also within the scope of the invention for the fluid to be pumped so as to flow up or through or across the solids digestion vessel if desired.

Connections are also made for the passage of gas from the fluids digestion vessel to the solids digestion vessel and vice versa. Gas preferably enters the solids digestion vessel via one or more spargers so as to agitate the contents of the solids digestion vessel over most or all of its volume. Excess of gas may be used for energy production, stored, discharged to atmosphere, or flared off. If the excess of gas is used for energy production, some or all of the energy produced may be used directly or indirectly to provide heat for the heating and cooling coil. For CHP it is preferred that the daily output of gas exceed about 1000 cubic meters.

The pH of the solid waste and/or the liquid waste may be adjusted to suit the bacteria which are carrying out the digestion, by the incorporation of suitable materials, for example ground chalk or lime. These materials may be added to the solids waste when it is loaded into the vessel at a first location remote from the fluids digestion vessel.

The solids digestion is carried out until the solid waste has been digested to a sufficient extent. This will usually be achieved when the solid is acceptable for direct discharge or use in the environment. After the solids digestion has been carried out sufficiently, the passage of fluid into the solids digestion vessel is halted, for example by disconnecting the connecting pipe, and fluid may be allowed to drain from the solids until the solid waste has reached a suitable consistency for handling. It is not essential for this further drainage to occur, and all connections may be disconnected immediately after sufficient digestion has occurred if desired.

After disconnection of the solids digestion vessel from the fluid source, the solids digestion vessel is transported to another location where it may be emptied and refilled with a further batch of solid waste.

Figure 2:
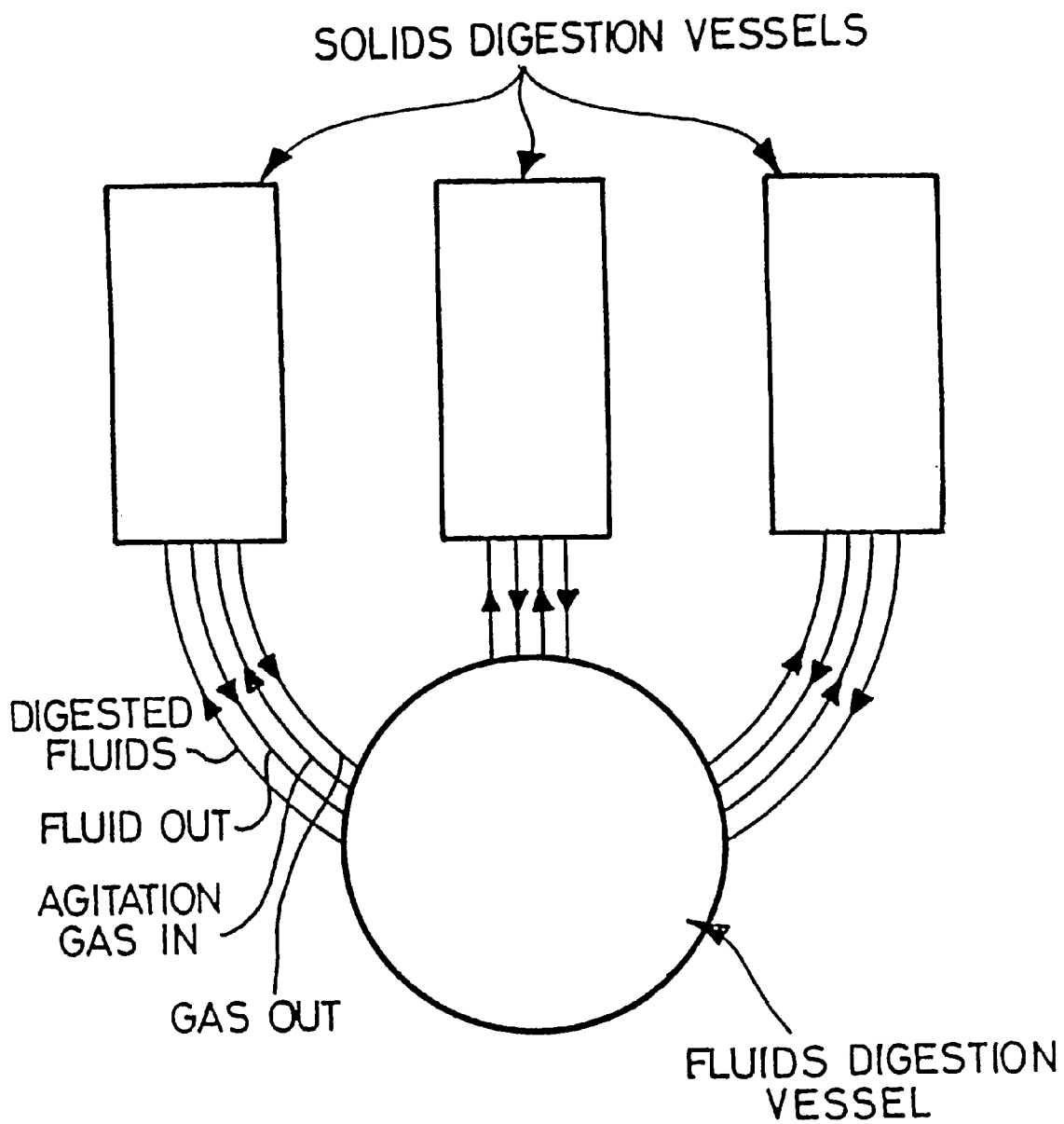
FIG. 2 is a diagrammatic flow diagram of the solid and fluid digestion stages of a process in accordance with an alternative embodiment of the invention.

A plurality of solids digestion vessels may be transported, separately or together, to the location of the fluid source as shown in FIG. 2. Here, three solids digestion vessels have been loaded with solids waste and transported to the location of the fluids digestion vessel. Each solids digestion vessel has been connected to the fluids digestion vessel by means of an umbilical connection which houses four pipe lines comprising: fluid in; fluid out; gas in; gas out. When the solids in a solids digestion vessel have been sufficiently digested, the umbilical connection is removed, and the solids digestion vessel is transported to another location, optionally after the removal of some or all digested solid waste material.

Figure 3:
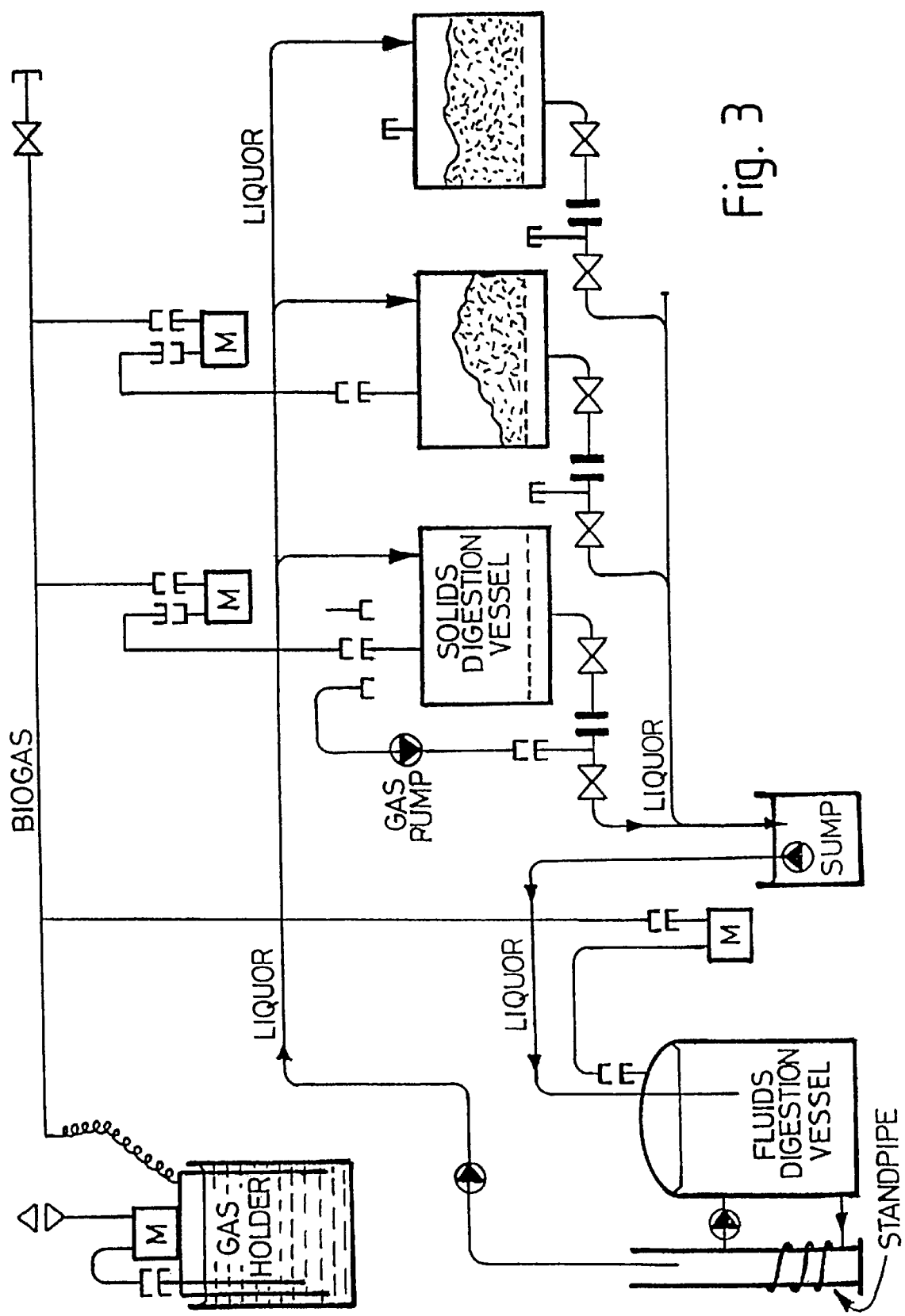
FIG. 3 is a diagrammatic flow diagram of another embodiment of a process in accordance with the present invention.

Referring now to FIG. 3, a fluids digestion vessel is permanently located underground, and it is connected to three solids digestion vessels. Each solids digestion vessel is detachable from the fluids digestion vessel and transportable.

Each solids digestion vessel is connected in the same way to the fluids digestion vessel, via a sump, and to a biogas line via a gas meter M. For simplicity all of the connections are illustrated for the left hand solids digestion vessel only.

Fluid waste is continuously recycled between the fluids digestion vessel and an adjacent standpipe, by means of a pump. A band heater is controlled by a thermostat to keep the fluid temperature in the standpipe at around 59° C., causing the temperature of fluid in the fluids digestion vessel to be around 55° C.

Fluid waste (liquor) is pumped out of the standpipe and distributed between the three solids digestion vessels. The liquor is shown here entering the top of the solids digestion vessels; however it could also be arranged to flow in through the bottom, to provide agitation and to unblock solids from the grid at the bottom of the vessel.

The top of the fluids digestion vessel is connected to the top of each solids digestion vessel by gas pipes. This allows equilibration of pressure in each vessel by passage of gas in either direction. Excess of biogas is collected in a gas holder (top left of diagram) or vented or connected to apparatus for gas use (top right of diagram).

Liquor which passes down through the solid waste in each solids digestion vessel is collected in a sump, from where it is pumped back into the fluids digestion vessel for the cycle to start again.

Occasionally, for example once a day, the solid waste is agitated by pumping gas through the liquor outlet piping in the bottom of the solids digestion vessel. This is done by closing off the valve in the liquor outlet which is closest to the sump, disconnecting the gas outlet from the biogas line, and connecting a gas pump between the gas outlet and the liquor outlet. Operation of the gas pump locally recycles gas through the grid at the bottom of the solids digestion vessel, causing agitation of the solids therein. On completion of the agitation the reverse procedure is followed to restore the fluid connections to their usual operative status as shown in the diagram.

A single gas pump may be used sequentially on any or all of the solids digestion vessels, or each vessel may be provided with a dedicated gas pump.

As an alternative to the use of a gas pump, agitation of the solids may be achieved by pumping liquor back from the sump through the liquor outlet pipes in each solids digestion vessel. This avoids the use of pressurised gas and is therefore preferred for safety reasons. The pumping may be steady or in pulses to achieve more vigorous agitation.

The gas outlet at the top of each solids digestion vessel may be connected to any one of three pipes (illustrated for the vessel on the left in FIG. 3). One pipe is a simple vent to atmosphere or for sampling or collection. A second pipe connects to the biogas line via a meter M. Each gas meter M may be used for measuring the rate of local gas production when liquid pumping is stopped. The third pipe is used for connecting the gas pump for agitation of the solid as described above. The three connections are shown separately for the purposes of illustration, but they could be combined together in a single housing and different connections made by means of a three way valve.

All of the fluid connections are snap tight valve connections. The valves are open when the connection is correctly made, but each half of the connection is sealed by a valve when not connected. It is preferred that the gas pipes are of different diameter than the liquid pipes, to avoid accidental connection of a gas pipe to a liquid pipe.

It is particularly preferred that the internal diameter of the gas piping is greater than that of the liquid piping for ease of flow. For example the gas pipes may be 25 mm and the liquid pipes may be 19 mm internal diameter.

Typically each solids digestion vessel is filled two-thirds to three-quarters full of solids waste at a remote location, for example an abattoir. After transportation to the site of the fluids digestion vessel it is filled with hot liquid from the fluids digestion vessel or the standpipe. The remaining connections are then made, and agitation is provided as required.

If aerobic digestion is required after completion of anaerobic digestion, this may readily be carried out by draining liquid waste from a solids digestion vessel, disconnecting the pipe connections, and blowing air through the liquor outlet pipe at the bottom of the solids digestion vessel.

The apparatus shown in FIG. 3 will digest a maximum of about 15,000 tonnes per annum of solids waste, and can economically digest 5,000 tonnes per annum or less. This compares to a fixed installation which would not economically be used to digest less than around 10,000 tonnes per annum.

The invention therefore provides a convenient method of treating solid and liquid wastes, which reduces the amount of handling of the untreated solid waste.

I claim:

1. A process for digesting solid waste material from a waste producer at a first location, which process comprises:
   a. collecting waste material containing biodegradable solids in a solids digestion vessel at the first location;
   b. transporting the solids digestion vessel to a second location at which is sited a source of organic material undergoing anaerobic bacterial digestion in a fluid phase digestion stage to produce a fluid fraction containing active bacteria;
   c. feeding at least part of the fluid fraction from the fluid phase digestion stage into the solids digestion vessel to provide at least part of a fluid phase in the solids digestion vessel;
   d. allowing the solid waste material to be digested to a sufficient extent;
   e. draining at least some of the fluid phase from the solids digestion vessel into the fluid phase digestion stage; and
   f. transporting the solids digestion vessel from the second location back to the first location,
   thereby ensuring that the waste producer receives back his own digested waste material uncontaminated with waste of unknown source or content.

2. The process of claim 1, wherein the waste is subjected to an additional stage of aerobic digestion.

3. The process of claim 1, wherein the solids digestion vessel is operated in the temperature range 40 to 65° C.

4. The process of claim 1, wherein the waste is heated during the transportation step b.

5. The process of claim 1, wherein a plurality of solids digestion vessels are connected to a single fluid phase digestion stage.

6. The process of claim 1, wherein the solids digestion vessel is connected to the fluid phase digestion stage by fluid or gas connections and all the fluid or gas connections between the solids digestion vessel and the fluid phase digestion stage are carried by a single connector.

* * * * *